US008859612B2

(12) United States Patent
Horcajada et al.

(10) Patent No.: US 8,859,612 B2
(45) Date of Patent: Oct. 14, 2014

(54) USE OF HESPERIDIN OR ONE OF ITS DERIVATIVES FOR MAKING A MEDICINE FOR BONE FORMATION STIMULATION

(75) Inventors: Marie-Noëlle Horcajada, Gerzat (FR); Véronique Coxam, Ceyrat (FR); Christine Morand, Crevant Laveine (FR); Marie-Jeanne Davicco, Chamalieres (FR)

(73) Assignee: Institut National de la Recherche Agronomique (INRA), Paris (FR)

( * ) Notice: Subject to any disclaimer, the term of this patent is extended or adjusted under 35 U.S.C. 154(b) by 1276 days.

(21) Appl. No.: 10/519,386

(22) PCT Filed: Jun. 27, 2003

(86) PCT No.: PCT/FR03/02005
§ 371 (c)(1),
(2), (4) Date: Dec. 27, 2004

(87) PCT Pub. No.: WO2004/002496
PCT Pub. Date: Jan. 8, 2004

(65) Prior Publication Data
US 2006/0034893 A1    Feb. 16, 2006

(30) Foreign Application Priority Data
Jun. 28, 2002   (FR) ...................... 02 08171

(51) Int. Cl.
*A61K 31/7048* (2006.01)
*A61K 31/353* (2006.01)
*A61P 19/08* (2006.01)
*A23L 1/30* (2006.01)

(52) U.S. Cl.
CPC ........... *A23L 1/3002* (2013.01); *A23V 2002/00* (2013.01)
USPC ................ 514/439; 514/25; 514/27; 424/439

(58) Field of Classification Search
USPC ................ 514/25, 27, 456; 424/439
See application file for complete search history.

(56) References Cited

U.S. PATENT DOCUMENTS

| 2,400,693 | A | 5/1946 | Higby |
| 2,442,110 | A | 3/1948 | Baier |
| 5,506,211 | A | 4/1996 | Barnes et al. |
| 5,559,146 | A | 9/1996 | Sablon |
| 5,763,414 | A | 6/1998 | Bok et al. |
| 6,048,712 | A | 4/2000 | Miyake et al. |
| 2001/0014669 | A1* | 8/2001 | Bok et al. ......................... 514/27 |
| 2001/0046977 | A1 | 11/2001 | Yates |
| 2002/0009510 | A1 | 1/2002 | Muhlbauer |
| 2002/0010341 | A1 | 1/2002 | Mesfin et al. |
| 2002/0035074 | A1 | 3/2002 | Kelly |

FOREIGN PATENT DOCUMENTS

| DE | 197 42 025 A1 | 9/1997 |
| EP | 0 210 728 A2 | 6/1986 |
| EP | 0 633 022 A2 | 6/1994 |
| EP | 0 719 544 A1 | 7/1996 |
| EP | 0 825 196 A2 | 2/1998 |
| EP | 0 938 899 A2 | 11/1998 |
| EP | 1 127 572 A2 | 8/2001 |
| GB | 486898 | 6/1938 |
| GB | 858784 | 1/1961 |
| JP | 8188593 | 7/1996 |
| JP | 2001114675 A * | 4/2001 |
| JP | 2001114675 A | 4/2001 |
| KR | 1020000058219 A | 9/2000 |
| WO | WO 98/16220 * | 4/1998 |
| WO | WO 99/21549 A1 | 5/1999 |
| WO | WO 02/17909 A1 | 3/2002 |

OTHER PUBLICATIONS

Wang et al, "Effect of *Drynaria baronii* Rhizome Extracts on the Proliferation in Osteoblast-Like UMR106 Cells", Pharmaceutical Biology, 2001, vol. 39, No. 4, pp. 259-262.*

* cited by examiner

*Primary Examiner* — Sreeni Padmanabhan
*Assistant Examiner* — Sahar Javanmard
(74) *Attorney, Agent, or Firm* — Jacobson Holman, PLLC

(57) ABSTRACT

The invention relates to the use of the compound hesperidin or of one of its derivatives for the manufacture of a composition designed to stimulate bone formation and/or inhibit bone resorption in man or animals.

20 Claims, 7 Drawing Sheets

USE OF HESPERIDIN OR ONE OF ITS DERIVATIVES FOR MAKING A MEDICINE FOR BONE FORMATION STIMULATION

This is a nationalization of PCT/FRO3/002005 filed Jun. 27, 2003 and published in French.

FIELD OF THE INVENTION

The invention relates to the field concerning the maintenance or reestablishment of the equilibrium in bone metabolism in man or animals, in particular for the prevention or the treatment of disorders linked to an imbalance of bone metabolism by means of nutritional intake or therapeutic administration of a composition stimulating bone formation and/or inhibiting bone resorption.

PRIOR ART

Bone is not a static tissue. Bone undergoes constant remodelling as a result of the destruction and de novo synthesis of bone tissue in a complex process involving two main types of cells, the osteoblasts which produce new bone tissue and the osteoclasts which destroy bone, respectively.

The activities of these cells are regulated by a large number of cytokines and growth factors, most of which have been identified and cloned, as has been described in the general review by Mundy (Mundy, G. R., 1996, Clin. Orthop., vol. 324: 24-28; Mundy, G. R., 1993, J. Bone Miner Res, vol. 8: S 505-S 510).

The osteoblasts, the cells responsible for bone formation, differentiate from precursor cells and express and secrete many enzymes and many structural proteins of the bone matrix, including collagen type I, osteocalcin, osteopontin and alkaline phosphatase (Stein G. et al., 1990, Curr. Opin Cell Biol. vol. 2: 1018-1027; Harris S et al. 1994, J. Bone Miner Res Vol. 9:855-863).

The osteoblasts also synthesise many growth regulatory peptides, including the BMP ("Bone Morphogenetic Proteins") peptides, which are stored in the bone matrix and which are probably responsible for normal bone formation.

Like alkaline phosphatase, osteocalcin and osteopontin, the BMP peptides are expressed by osteoblasts in culture at the time when these cells proliferate and differentiate.

The osteoclasts are multinucleated cells which are responsible for bone loss in a process generally designated bone resorption.

In a healthy adult, man or animal, the joint action of the osteoblasts and osteoclasts makes possible the maintenance of the bone mass over time and simultaneously ensures remodelling of bone tissue by resorption and de novo synthesis of bone.

In a healthy adult, the rate of formation of the osteoclasts and osteoblasts is such that a balance is struck between bone formation and bone resorption. However, in osteoporotic individuals, an imbalance in the process of bone remodelling is produced which culminates in a loss of bone which proceeds at a more rapid rate than the rate of formation. Although this imbalance exists to a certain extent in most individuals as they age, it is much more severe and occurs at a younger age in osteoporotic individuals.

Thus, in man and other mammals a great variety of disorders are related to abnormal metabolism of bone resorption and bone formation, leading to an imbalance in metabolism or bone remodelling.

In particular, a great heterogeneity is observed in the value of the peak bone mass depending on the individuals, this heterogeneity being due to large variations in the process of bone growth from a very young age. Thus, the maximal bone mass attained on reaching adulthood, consequently designated peak bone mass, is very variable from one individual to another. As they grow old, the individuals who possess a low value for the peak bone mass and who undergo bone loss due to ageing are at a disadvantage. Thus, irrespective of the individual, an early preventive treatment of bone loss is recommended, so as to reduce as much as possible the imbalances in bone remodelling which are produced in a non-pathological manner with ageing, in particular the risks of premature bone fractures.

Of the pathological disorders related to an imbalance in bone metabolism, particular mention may be made of the disorders or diseases such as osteoporosis, Paget's disease, bone loss or osteolysis observed close to a prosthesis, metastatic bone diseases, hypercalcemia due to a cancer, multiple myelomas and periodontal diseases.

Some of the disorders or diseases of bone metabolism may be caused by long-term immobilisation, for example long-term hospitalisation or even after a period of weightlessness.

Of the disorders linked to abnormal bone resorption, the most common is osteoporosis, the most frequent manifestation of which is observed in women after the start of menopause. Osteoporosis is a systemic skeletal disease characterised by a reduction of the bone mass and a deterioration of the microarchitecture of bone tissue, associated with an increase of the fragility of the bone and its susceptibility to fracture.

There are other factors likely to increase bone loss leading to osteoporosis, such as the consumption of cigarettes, alcohol abuse, a sedentary life style, a low calcium intake, an unbalanced diet or also vitamin D deficiency.

Since osteoporosis, like other disorders associated with bone loss, constitutes a chronic disorder, its prevention and its treatment must be planned in the long term.

It is currently accepted that early treatment must be preferred because the two critical phases for bone capital are:
the period of growth during which the maximal bone mass (peak bone mass) is acquired;
ageing which conditions the rate of loss of bone mass.

The prevention of osteoporosis must hence no longer be restricted to the elderly individual.

Moreover, in man and animals, there are many conditions characterised by the need to increase bone formation. For example, in the case of bone fractures, it is necessary to stimulate bone growth in order to accelerate complete repair of the bone. This need is also present in the periodontal diseases, the metastatic diseases of bone, the osteolytic diseases and the conditions under which repair of the connective tissue is required, for example for the cicatrisation or regeneration of defects or traumatisms of cartilage. The stimulation of bone growth is also required in the case of primary and secondary hyperparathyroidism, as well as in osteoporosis associated with diabetes and in osteoporosis associated with glucocorticoids.

To-day there are many compounds active on the stimulation of bone formation or the inhibition of bone resorption, among which mention may be made of the family of the polyphosphonate compounds (European patent No. EP 210 728), the thioamide oxazolidinones (U.S. patent application published under No 2002/0010341), the amino bis-phosphonate compounds (U.S. patent application published under No 2001/0046977) or also the isoflavone compounds (U.S. patent application published under No 2002/0035074). The use of a plant extract of the *Lycopersicon* genus has also been suggested (U.S. patent application published under No 2002/0009510).

Although there exists to-day a large variety of active compounds for stimulating bone formation and/or inhibiting bone resorption, there is a constant need for new active compounds, in particular owing to the limited success of the current treatments.

Furthermore, in view of the chronic character of some conditions caused by an imbalance in bone metabolism, there is a need for new active compounds which it will be possible to use in the long term in man and animals, and which are likely to be available in the form of a food additive, for example in the form of a nutritional composition.

SUMMARY OF THE INVENTION

In a surprising manner, the applicant has shown that hesperidin, which is a compound of the flavonoid family, is capable of acting on bone metabolism by stimulating bone formation and inhibiting bone resorption.

Hence, a nutritional composition and a pharmaceutical composition for human or veterinary use comprising, as active ingredient, the compound hesperidin or one of its derivatives is provided according to the invention.

The invention also relates to the use of the compound hesperidin or of one of its derivatives for the manufacture of a composition designed to stimulate bone formation and/or inhibit bone resorption in man and animals, in particular the dog, the cat or the horse.

According to a first feature, the above use is characterised in that the said composition is a nutritional composition suitable for oral administration.

According to a second feature, the above use is characterised in that the said composition is a pharmaceutical composition for oral, parenteral or intravenous administration.

DETAILED DESCRIPTION OF THE INVENTION

Figure 1:
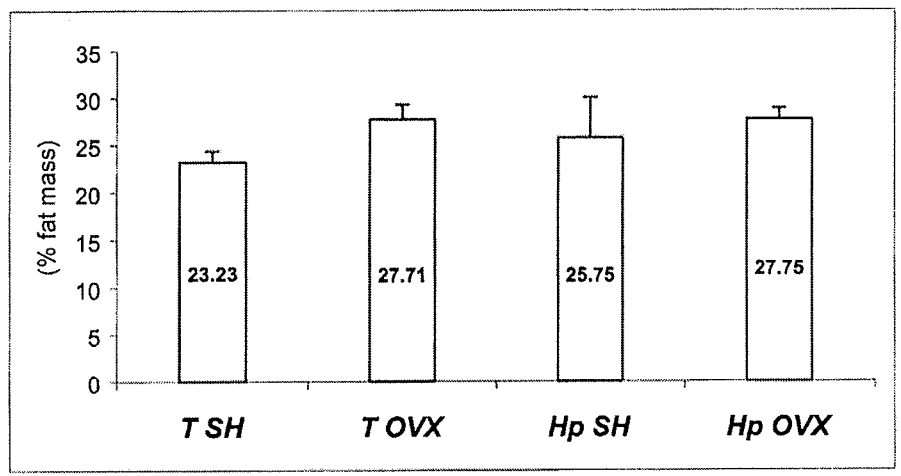
FIG. 1 illustrates the maintenance of an equivalent body composition (% of fat mass compared to body weight) between different groups of animals, normal animals (TSH), oophorectomised animals (TOVX), normal animals treated with hesperidin (HpSH) and oophorectomised animals treated with hesperidin (HpOVX). The fat mass percentage is shown along the ordinate.

According to the invention, a nutritional composition and a pharmaceutical composition for human or veterinary use are provided which are designed to stimulate bone formation and/or inhibit bone resorption in man or animals and which contain, as active ingredient, the compound hesperidin or one of its derivatives.

Hesperidin is a naturally occurring glucoside compound found principally in citrus fruit, i.e. the fruits of the *Citrus* genus. The majority of the hesperidin is present in the peel of the citrus fruits but it is also found in large quantities in the pulp and hence the juice of the citrus fruits, including oranges and lemons.

Hesperidin is a glucosylated compound comprising a flavanone nucleus of hesperetin (3',5',5-trihydroxy-4'-methoxy-flavanone) to which is covalently linked a glucoside moiety of rutinose, L-rhamnosyl-(α 1→6)-glucose), bound to the hydroxyl group present on the carbon at position 7 of hesperetin.

The compound hesperidin is a compound of the flavonoid family which is currently used in combination with vitamin C in order to potentiate the biological activity of vitamin C, in particular by reducing the denaturation of vitamin C as a result of oxidation. In this application, hesperidin is suggested as an auxiliary agent in the treatment of cardiovascular diseases, in particular of hypertension and haemorrhages.

Hesperidin has also been described as a chondro-protective agent owing to its capacity to inhibit the destruction of the matrix of chondrocytes derived from cartilage (patent application No EP 633 022).

Hesperidin has also been suggested in the prior art as an agent for the prevention of the pigmentation of the skin (German patent application No DE 19742 025), as an inhibitor of HMG-CoA reductase (U.S. Pat. No. 5,763,414) or of acyl CoA-cholesterol-O-acyl transferase (PCT application No WO 99/21.549) or also of platelet aggregation (Korean patent application No KR 276 979.

In a surprising manner, it has been shown according to the invention that hesperidin stimulates bone formation and inhibits bone resorption.

As is illustrated by the examples, hesperidin induces an increase in the density of metaphyseal bone tissue (trabecular bone) and in the density of the diaphyseal bone (cortical bone), thus inducing an improvement in bone mineralisation.

Hesperidin also stimulates bone accretion as is shown by the marked increase of the plasma levels of osteocalcin observed in the animals which have received food supplemented with this compound.

It has also been shown that hesperidin causes a stop to the multiplication of osteoblast precursor cells and brings about their differentiation to mature osteoblasts, as is visualised by the induction of an increase in the activity of alkaline phosphatase. Similarly, hesperidin induces an increase in the accumulation of calcium in the osteoblasts.

In addition, hesperidin inhibits bone resorption in oophorectomised rats, which is the reference experimental animal model mimicking human osteoporosis.

In particular, it has been shown according to the invention that hesperidin makes possible the maintenance of bone capital in the course of ageing in the individuals which have terminated their growth, in particular in individuals in a situation of hormonal deficiency, as is observed in the 6 months old oophorectomised rats, which are a model mimicking the physiological situation of menopause.

These two related activities of hesperidin on bone formation and the inhibition of bone resorption respectively confer on it great utility as a compound active in man or animals for maintaining or re-establishing the balance in bone metabolism, i.e.:
  either by maintaining constant over time, with age, the activities of the osteoblast and osteoclast cells and thus preventing disorders of bone metabolism;
  or by rectifying an imbalance in bone metabolism, for example in disorders like osteoporosis or also by stimulating bone regeneration for example in the case of infraction or fracture of bone.

Thus, the object of the present invention is the use of the compound hesperidin or of one of its derivatives for the manufacture of a composition capable of maintaining or re-establishing the balance in bone metabolism in man or animal by stimulating bone formation and/or by inhibiting bone resorption.

By hesperidin is meant the compound (S)-7-[[6-0-(6-deoxy-α-L-mannopyranosyl)-β-D-glucopyranosyl]oxy]-2,3-dihydro-5-hydroxy-2-(3-hydroxy-4-methoxyphenyl)-4H-1-benzopyran-4-one.

By "derivative" of hesperidin, is meant according to the invention the following compounds:
  the compound hesperetin, consisting of the non-glycosylated flavanone nucleus of hesperidin, which has the following formula: (S)-2,3-dihydro-5,7-dihydroxy-2-(3-hydroxy-4-methoxyphenyl)-4H-1-benzopyran-4-one; 3',5,7-trihydroxy-4'-methoxyflavanone;
  α-glucosyl-hesperidin, which bears a chain of 1 to 20 glucose residues joined together by a 1,4-link, the chain of glucose residues being itself attached by a linkage of the 1,4 type to position 4 of the glucose residue of hesperidin; these derivatives of hesperidin and the procedure for their preparation are described in particular in the patent application No EP 0 825 19 and in the U.S. Pat. No. 6,048,712;
  the methyl-hesperidin compounds, in particular the compound $3^1$-methyl-7-(rhamnosyl-2-methyl-glucosyl) hesperidin and the compound $3^1$-methylhesperidin, these compounds as well as the procedure for their preparation being described in the U.S. Pat. No. 858,784;
  the conjugates of hesperetin and sulfate or glucuronide, which are found with hesperetin as products of the metabolism of hesperidin in the systemic circulation.

By "stimulation of bone formation" is meant according to the invention, the capacity of hesperidin or of one of its derivatives to stimulate the activity of osteoblasts and thus promote the synthesis of the protein network of bone and the deposition of minerals, in particular calcium, in this protein network, i.e. to stimulate the mineralisation of the bone, also called bone accretion.

In order to verify that the supply of hesperidin to man or animals, in particular a mammal, stimulates the formation of bone, the specialist skilled in the art will be able to have recourse in particular to conventional densitometry measurements and to verify that the supply of hesperidin or of one of its derivatives induces an increase of the bone density at a given dose.

The specialist skilled in the art may also have recourse to any of the other tests also described in the examples, such as the measurement of the resistance of bone to rupture or also to the measurement of alkaline phosphatase activity and the measurement of the accumulation of calcium in the osteoblast cells.

By "inhibition of bone resorption" is meant according to the invention inhibition of the destructive activity of bone tissue by the osteoclast cells. In order to verify that the supply of hesperidin or of one of its derivatives in man or animals inhibits bone resorption, the specialist skilled in the art can measure the urinary excretion of desoxypyridinoline as described in the examples, a diminution of the expression of desoxypyridinoline being the reflection of inhibition of bone resorption.

The supply of hesperidin or of one of its derivatives to an animal organism induces simultaneously a stimulation of bone formation and inhibition of bone resorption, the overall increase of bone mineralisation, and hence of the bone density, being the result of the induction of these two mechanisms.

In order to determine whether a subject presents a state of reduced bone mass and as a consequence requires a supply of hesperidin or of one of its derivatives, the specialist skilled in the art will be able to refer in particular to the report of the World Health Organisation (WHO) of 1994 entitled "Assessment of fracture risk and its application to screening for post-menopausal osteoporosis" (WHO Technical Series-843).

A nutritional composition or a therapeutic composition containing hesperidin or one of its derivatives as active ingredient is designed in the first instance for the prevention of bone loss due to an imbalance in the remodelling of bone tissue in man or animals in particular in a non-human mammal, in particular a domestic mammal like a dog or a cat or even a horse, in particular a thoroughbred.

A composition such as defined above is also designed to promote bone growth in young individuals in order to obtain individuals possessing high bone density and, if possible, concomitantly a high peak bone mass. In particular, a composition according to the invention is useful during the growth phase of man as well as other mammals, in particular of pedigree dogs, and also racehorses.

The composition containing hesperidin or one of its derivatives is also designed for Individuals presenting symptoms of bone deficit or likely to suffer from bone deficit, i.e. from an imbalance in the relationship between bone formation and bone resorption which, if it continues, induces a diminution of the bone mass. A composition according to the invention is also designed for individuals presenting symptoms of bone deficit resulting from a fracture, an operation or also a dental disease.

In particular, a nutritional or pharmaceutical composition designed for human or veterinary medicine according to the invention is useful in the treatment of diseases such as osteoporosis, Paget's disease, bone loss or osteolysis observed close to a prosthesis, metastatic bone diseases, hypercalcemia due to a cancer, multiple myelomas, periodontal diseases or also osteoarthritis.

The composition according to the invention may be available in the form of a nutritional composition or also in the form of a pharmaceutical composition, as is described hereafter.

It has also been shown according to the invention that hesperidin induces the cessation of the multiplication and causes the differentiation of osteoblast cells without requiring the presence of auxiliary agents such as osteoblast differentiation factors like vitamin D3 and dexamethasone, contrary to many anti-osteoporosis compounds described in the prior art. This experimental observation emphasizes the value of hesperidin and its derivatives for stimulating bone formation or inhibiting bone resorption, because these compounds are biologically active when used on their own and consequently do not require to be supplied to the organism in the form of a combination of hesperidin or of one of its derivatives with another compound such as a vitamin.

In addition, the fact that hesperidin induces an increase not only of the trabecular bone density but also of the cortical bone density demonstrates the high level of biological activity of this molecule. In fact, the trabecular bone, which forms the head of the bone and which is extensively vascularised is the preferred site of the exchanges of calcium between the bone and the systemic circulation, whereas the cortical bone which forms the straight body of the bone and which is vascularised only to a slight extent, is much less likely to be affected rapidly by a change in its mineralisation.

Nutritional Compositions Containing Hesperidin or One of its Derivatives

As has already been mentioned above, many disorders linked to an imbalance of bone metabolism, such as osteoporosis, develop gradually over a long period of time and require chronic treatments. Their prevention or their treatment can hence be carried out by means of a regular supply of hesperidin or of one of its derivatives, preferably in the form of a nutritional composition.

Similarly, a regular nutritional supply of hesperidin to young growing individuals, humans or animals is such as to make possible the production of a high bone density and an elevated peak bone mass by stimulation of bone formation when these individuals attain adult age.

A regular nutritional supply of hesperidin is also useful for preventing the bone loss that occurs with ageing.

The object of the invention is also a nutritional composition for stimulating bone formation and/or inhibiting bone resorption, characterised in that it contains, as active nutritional compound, the compound hesperidin or one of its derivatives.

By "nutritional composition" is meant according to the invention, a composition containing hesperidin or one of its derivatives and constituting a dietary composition or even a dietary supplement not possessing the characteristics of a medicine.

The different uses of the compound hesperidin or of one of it derivatives for the manufacture of a nutritional composition will be defined hereafter in relation to the technical characteristics of the said nutritional composition.

A nutritional composition according to the invention is preferably suitable for oral administration.

According to a first feature, a nutritional composition according to the invention is a dietary food used for the maintenance of the good health of humans or animals who ingest it. Such a nutritional composition is also commonly designated "functional food", which is designed to be consumed either as an integral part of the diet or as a food supplement, but whose content of hesperidin or one of its derivatives implies a physiological role exceeding the supply of basic nutrient needs.

According to a first feature, the said nutritional composition is designed to stimulate bone formation in young individuals in the growth phase.

According to a second feature, the said nutritional composition is designed to prevent the bone loss that occurs with ageing.

According to a third feature, the said nutritional composition is designed to prevent or treat disorders linked to an imbalance in the relationship between bone formation and bone resorption.

According to a fourth feature, the said nutritional composition is designed to treat a bone defect resulting from a fracture.

According to yet another feature, the said nutritional composition is designed to prevent or treat diseases selected from osteoporosis, Paget's disease, bone loss or osteolysis observed close to a prosthesis, metastatic bone diseases, hypercalcemia due to a cancer, multiple myelomas, periodontal diseases or osteoarthritis.

A nutritional composition according to the invention, characterised in that it comprises the compound hesperidin or one of its derivatives as active ingredient may be available in a great variety of forms of food compositions and drinks, including juices, preferably fruit juices, yoghurts, ice creams, cheeses, baked goods such as bread, biscuits and cake, dairy products, desserts, confectionery products, cereal bars, breakfast cereals, food seasoning products (in particular spices and sauces), fruit salads, stewed fruit, etc.

A nutritional composition according to the invention, characterized in that it comprises the compound hesperidin or one of its derivatives as active ingredient may also be available in a great variety of products designed as animal foodstuffs, in particular for the dog or the cat, whether in a wet form, semi-wet form or dry form, in particular in the form of croquettes.

As already described previously, hesperidin is a naturally occurring compound in citrus fruits of the *Citrus* genus, in particular in oranges and lemons, the majority of this compound being contained in the peel, but significant quantities are also found in the pulp, as has been described in particular by MANSELL et al. (MANSELL R. L. et al., 1983, J. Agric.

Food Chem., vol. 31: 156-162), ROUSEFF et al. (ROUSEFF R. L. et al., 1987, J. Agric. Food Chem., vol. 35:1027-1030) or also GIL-IZQUIERDO et al. (GIL-IZQUIERDO A et al., 2001, J. Agric. Food Chem., vol. 49: 1035-1041).

According to a first feature, a nutritional composition according to the invention may be available in the form of a citrus juice, in particular orange juice or lemon juice, where appropriate in the form of a citrus juice concentrate.

According to a second feature, a nutritional compound according to the invention may consist of a food composition enriched with citrus fruit or an extract of citrus fruit, in particular orange or lemon.

According to a third feature, a nutritional composition according to the invention is available in the form of any product, in particular any drink, flavoured with citrus fruit peel, citrus fruit juice, citrus fruit pulp or any other citrus extract, including oranges and lemons.

Thus, a nutritional composition according to the invention, which is available in a liquid or solid form, in particular in the form of a powder, may consist of an extraction product obtained from the peel or pulp of a citrus fruit, or also comprise an extraction product obtained from the peel or pulp of a citrus fruit.

In particular, a nutritional composition according to the invention is available in the form of a drink, for example mineral water, to which has been added an extract of the peel or pulp of a citrus fruit, including an orange or a lemon.

According to yet another feature, the extraction product may be initially enriched with hesperidin if a specially adapted extraction procedure is utilised in order to attain such an objective, such as the procedure described in the Japanese patent application No JP 8 188 593, in which the product obtained after pressing the fruit of the *Citrus* genus is adjusted to pH 11.5-12.5, then the liquid obtained after pressing and adjustment of the pH is centrifuged, prior to a second pH adjustment to pH 5-5.5, followed by heating and a last centrifugation step prior to the recovery of the product enriched with hesperidin. Another extraction procedure that can be used for obtaining an extract enriched in hesperidin is that described in the British patent application No GB 486.898.

In order to obtain an extraction product enriched with hesperidin starting from citrus fruit, and more specifically from oranges or lemons, the specialist skilled in the art will also be able advantageously to refer to the procedures described respectively in the U.S. Pat. Nos. 2,400,693 and 2,442,110.

According to another feature, in a nutritional composition according to the invention, hesperidin or one of its derivatives is produced by chemical synthesis.

Preferably, a nutritional composition according to the invention comprises a quantity of the compound hesperidin or one of its derivatives suitable for a daily oral administration included between 0.01 mg and 500 mg.

For consumption by humans, a nutritional composition according to the invention comprises a quantity of active ingredient provided by the said composition that is adapted to a daily supply of hesperidin or of one of its derivatives included between 0.01 mg and 500 mg, preferably between 0.1 mg and 500 mg and very preferably between 1 mg and 500 mg.

For consumption by an animal, specifically a non-human mammal, including the dog, the cat or the horse, a nutritional composition according to the invention is adapted to a daily administration of active ingredient, provided by the said composition, included between 1 mg and 500 mg, preferably between 10 mg and 500 mg of hesperidin or one of its derivatives.

As an illustration, a mineral water supplemented with hesperidin or one of its derivatives will contain from 0.01 mg to 500 mg of active ingredients per liter, by estimating the daily mean human consumption of mineral water as being about 1 liter.

According to yet another feature, the above nutritional composition may comprise other nutritional compounds in combination with hesperidin or one of its derivatives.

Thus, the nutritional composition according to the invention may also comprise a source of calcium, for example in the form of a physiologically acceptable organic or inorganic compound such as inorganic calcium salts (calcium chloride, calcium phosphate, calcium sulfate, calcium oxide, calcium hydroxide or calcium carbonate) or organic constituents containing calcium such as skim milk powder, calcium caseinate or also organic salts of calcium (calcium citrate, calcium maleate or their mixtures).

The quantity of calcium contained in a nutritional composition according to the invention is adapted for a daily administration, provided by the said composition, included between 100 mg and 1000 mg, preferably between 200 mg and 700 mg and very preferably between 300 mg and 600 mg of calcium.

A nutritional composition according to the invention may also comprise vitamins such as vitamin A, vitamin D, vitamin E, vitamin K, vitamin C, folic acid, thiamine, riboflavin, vitamin $B_6$, vitamin $B_{12}$, niacin, biotin or also pantothenic acid.

A nutritional composition according to the invention may also comprise mineral elements and trace elements such as sodium, potassium, phosphorus, magnesium, copper, zinc, iron selenium, chromium and molybdanum.

It may also comprise soluble fibres such as agar-agar, an alginate, carob bean, carragheenan, gum arabic, guar gum, karaya gum, pectin or xanthan gum, these soluble fibres being in a hydrolysed or non-hydrolysed form.

It may also comprise compounds which are sources of energy, in particular one or more sources of carbohydrates selected from maltodextrins, starch, lactose, glucose, sucrose, fructose, xylitol and sorbitol.

In addition, a nutritional composition according to the invention may also comprise natural or artificial flavours, for example fruit flavours like banana, orange, peach, pineapple or raspberry or other plant flavours like vanilla, cocoa, coffee, etc.

As already mentioned previously, a composition designed to stimulate bone formation or to inhibit bone resorption according to the invention may also be available in the form of a pharmaceutical composition, as described hereafter.

Human Pharmaceutical or Veterinary Compositions According to the Invention

The object of the invention is also a human pharmaceutical or veterinary composition to stimulate bone formation and/or inhibit bone resorption, characterised in that it comprises, as active ingredient, the compound hesperidin or one of its derivatives.

In particular, the invention relates to the use of hesperidin or of one of its derivatives for the manufacture of a pharmaceutical composition for human use or a veterinary composition for the prevention or treatment of a disease linked to an imbalance in bone metabolism, i.e. a pharmaceutical composition capable of stimulating bone formation and/or inhibiting bone resorption.

The uses of hesperidin for the manufacture of a pharmaceutical composition will be described in relation to the technical characteristics of the said pharmaceutical composition hereafter.

A pharmaceutical composition according to the invention comprises as active ingredient hesperidin or one of its derivatives in a quantity suitable for stimulating bone formation or inhibiting bone resorption in individuals requiring such treatment.

According to a first feature, a pharmaceutical composition according to the invention is useful for stimulating bone formation in young individuals, humans or animals, in the growth phase, in order to increase the bone density attained at the beginning of adult age and to increase the maximal bone mass (peak bone mass) at the beginning of adult age.

According to a second feature, a human pharmaceutical or veterinary composition according to the invention is useful for preventing the bone loss that occurs with age, in the course of ageing.

According to a third feature, a human pharmaceutical or veterinary composition according to the invention is useful for preventing or treating disorders or diseases linked to an imbalance in the relationship between bone formation and bone resorption.

According to a fourth feature, a human pharmaceutical or veterinary composition according to the invention is useful for treating a bone deficit resulting from a fracture.

According to a fifth feature, a human pharmaceutical or veterinary composition according to the invention is useful in the treatment of diseases linked to an imbalance in bone remodelling such as osteoporosis, Paget's disease, bone loss or osteolysis observed close to a prosthesis, metastatic bone diseases, hypercalcemia due to a cancer, multiple myelomas, periodontal diseases or also osteoarthritis.

It may be a human pharmaceutical or veterinary composition, in particular for the dog or the cat or even the horse, in particular the thoroughbred.

The pharmaceutical composition according to the invention is available in a form for oral, parenteral or intravenous administration.

In the form designed for its administration to humans a pharmaceutical composition according to the invention advantageously comprises a quantity of hesperidin or of one of its derivatives adapted to a daily administration of the active ingredient, provided by the said composition, included between 0.01 mg and 500 mg.

In the form designed for administration to animals, particularly a domestic mammal such as the dog or the cat, a pharmaceutical composition according to the invention comprises a quantity of hesperidin or of one of its derivatives adapted to a daily administration of the active ingredient, provided by the said composition, included between 1 mg and 5.00 mg.

A pharmaceutical composition according to the invention comprises hesperidin or one of its derivatives in combination with at least one excipient selected from the group constituted by the pharmaceutically acceptable excipients.

Procedures for the preparation of pharmaceutical compositions according to the invention can easily be found by the specialist skilled in the art, for example in the handbook Remington's Pharmaceutical Sciences, Mid. Publishing Co, Easton, Pa., USA.

Physiologically acceptable excipients, vehicles and adjuvants are also described in the handbook entitled "Handbook of Pharmaceutical Excipients, Second edition, American Pharmaceutical Association, 1994.

In order to formulate a pharmaceutical composition according to the invention, the specialist skilled in the art will advantageously be able to refer to the latest edition of the European Pharmacopoeia or the Pharmacopoeia of the United States of America (USP).

The specialist skilled in the art will in particular be able advantageously to refer to the fourth edition "2002" of the European Pharmacopoeia or also to the edition USP 25-NF 20 of the American Pharmacopoeia (U.S. Pharmacopoeia).

Advantageously, a pharmaceutical composition such as defined above is suitable for oral, parenteral or intravenous administration.

When the pharmaceutical composition according to the invention comprises at least one pharmaceutically or physiologically acceptable excipient, it is in particular an excipient appropriate for administration of the composition by the oral route or an excipient suitable for administration of the composition by the parenteral route.

The invention also relates to a method for preventing or treating a disorder linked to an imbalance in bone metabolism, in particular a disorder associated with loss of bone mass, the said method comprising a step in the course of which a therapeutically efficacious quantity of hesperidin or of one of its derivatives or also a pharmaceutical composition containing hesperidin or one of its derivatives is administered to the patients.

A pharmaceutical composition comprising hesperidin or one of its derivatives according to the invention is available indifferently in a solid or liquid form.

For oral administration, a solid pharmaceutical composition in the form of tablets, capsules or gelatine capsules will be preferred.

In liquid form, a pharmaceutical composition in the form of an aqueous or non-aqueous suspension, or also in the form of a water-in-oil or oil-in-water emulsion will be preferred.

Solid pharmaceutical forms may comprise, as vehicles, adjuvants or excipients, at least one diluent, one flavour, one solubilising agent, one lubricant, one suspension agent, one binder, one disintegrating agent and one encapsulating agent.

Such compounds are for example magnesium carbonate, magnesium stearate, talc, lactose, pectin, dextrin, starch, gelatine, cellulosic materials, cocoa butter, etc.

The compositions in liquid form may also comprise water, possibly as a mixture with propylene glycol or polyethylene glycol, and possibly also colouring agents, flavours, stabilisers and thickening agents.

For the manufacture of a pharmaceutical composition according to the invention, hesperidin or one of its derivatives may be prepared in conformity with the teaching of the different patent documents cited previously in the description.

Preferably a pharmaceutical grade product containing hesperidin in a pure or practically form such as the hesperidin sold by the company NINGBO LIWAH PHARMACEUTICAL Co Ltd., belonging to the SANJIU ENTERPRISE GROUP, which comprises 95% by weight of hesperidin in ethyl acetate, will be used as the source of hesperidin.

In addition, the invention is illustrated without being limited by the following examples.

Example 1

Effect of Hesperidin on Bone Metabolism in the Oophorectomised Rat

The objective of this set of experiments was to test the impact of hesperetin on the bone metabolism of the oophorectomised rat (OVX) in comparison with that of sham-operated control rats (SH). Hesperetin is a flavanone, the glycosylated form of which (hesperidin) is specific for citrus fruit, and more particularly for the orange. This flavonoid is not present in other plant products. It is in the form of hesperidin that the experimental diets were supplemented.

A. Material and Methods

In order to study the possible impact of this molecule on bone tissue, 40 female 3 months old Wistar rats (266±2 g) were used. These animals were accustomed to a basic semi-synthetic diet for the 7 days preceding the start of the period of experimentation. At D0, 20 rats were sham-operated, the other 20 were oophorectomised. Distributed in groups of 10, they were fed on various diets for 3 months, at the end of which they were sacrificed. The last week before being killed, from D85 to D90, the rats were inspected and the urine was collected (over a period of 24 hours). Similarly, the body composition of the rats was measured. After being killed the plasma and the femurs were collected for different analyses [Femurs: resistance to rupture, densitometry; Plasma: osteocalcinemia (marker for osteoblast activity), hesperetin level: Urines: desoxypyridinoline (marker for bone resorption)]. Throughout the entire duration of the experimentation, the rats were weighed once a week. The daily quantity of food distributed to each animal was 20 g.

Distribution in Groups

10 T SH and 10 T OVX: sham-operated and oophorectomised rats receiving a standard control diet for 3 months 10 Hp SH et 10 Hp OVX: sham-operated and oophorectomised rats receiving a standard control diet supplemented with hesperidin (0.5%) for 3 months

B. Results

B.1 Change in Weight and Body Composition

The results are presented in FIG. 1. The values are expressed as means±SD. The rats showed a standard change in weight. Although at the end of the experimental period the body weight (g) of the OVX animals was significantly higher than that of the sham-operated animals [T SH: 326.6±9.4; T OVX: 363.3±7; Hp SH: 335.4±15.4; Hp OVX: 406.3±12.7], no significant difference concerning the body composition (% fat mass with respect to total body weight) was observed between the groups.

B.2 Uterine Weight

The uterine weight was evaluated in order to validate the castration. The oophorectomy effectively induced an atrophy of this organ (mg), by comparison with SH ($p<0.01$). Since this parameter was not modified by the consumption of hesperidin, this molecule thus seems to lack a uterotrophic effect.

TABLE 1

| T SH | T OVX | Hp SH | Hp OVX |
|---|---|---|---|
| 1031.9 ± 82.3 | 139.6 ± 10.2** | 659.4 ± 8.96 | 238.6 ± 2.23** |

B.3 Femoral Biomechanics

The diameter and length (mm) of the femurs were not significantly modified by the treatment.

TABLE 2

| Femoral resistance to rupture: | | | |
|---|---|---|---|
| T SH | T OVX | Hp SH | Hp OVX |
| 109.5 ± 3.3 | 102.2 ± 2.9 | 106.3 ± 5.3 | 11 2.4 ± 3.4 |

Although oophorectomy did not significantly diminished the femoral resistance to rupture (N), the oophorectomised rats receiving a diet supplemented with hesperidin show a tendency to improve this parameter.

B.3 Densitometry

The densities are expressed in g/cm$^2$.

TABLE 3

| Total femoral density (T-BMD) | | | |
|---|---|---|---|
| T SH | T OVX | Hp SH | Hp OVX |
| 0.2262 ± 0.0056 | 0.2143 ± 0.0025$^{ab}$ | 0.2501 ± 0.0028$^c$ | 0.2445 ± 0.0052 |

Oophorectomy induces a significant diminution of the total femoral density of the rats receiving the control diet compared to the sham-operated animals. On the other hand, the consumption of hesperidin completely prevents this demineralisation and, in addition, significantly improves this parameter in the SH.

Figure 2:
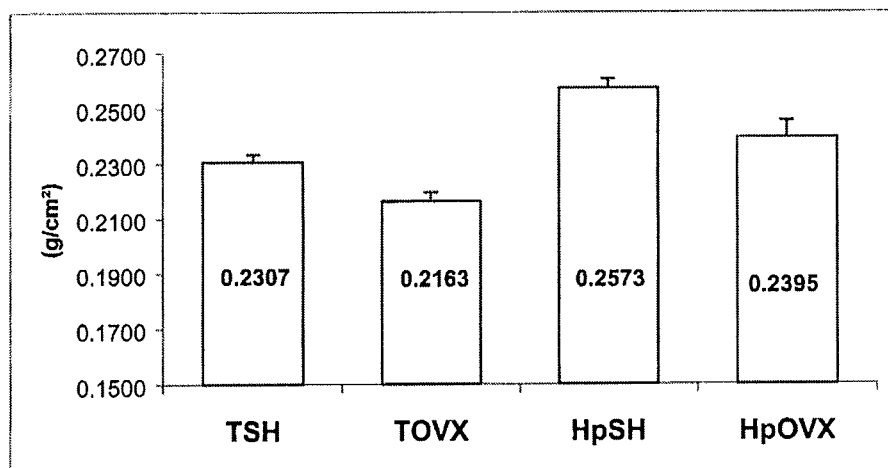
FIG. 2 illustrates the increase of the metaphyseal femoral density in intact or oophorectomised rats receiving the hesperidin diet in comparison with those subjected to a standard diet. The bone density in $g/cm^3$ is shown along the ordinate.

Metaphyseal Femoral Density (M-BMD) (FIG. 2)

The results relating to the whole femur are also confirmed at the metaphyseal zone essentially constituted of trabecular bone. The improvement of the mineralisation in the non-castrated animals which consumed the molecule was also demonstrated (by comparison with the T SH).

Diaphyseal Femoral Density (M-BMD):

The diaphyseal zone is constituted of cortical bone.

TABLE 4

| T SH | T OVX | Hp SH | Hp OVX |
|---|---|---|---|
| 0.2019 ± 0.0044 | 0.2003 ± 0.0032 | 0.2245 ± 0.0020* | 0.2258 ± 0.0055* |

The consumption of hesperidin significantly improves ($p<0.05$) this parameter in comparison to the other groups receiving a standard diet, in both the OVX and SH rats.

B.4 Bone Biomarkers

Figure 3:
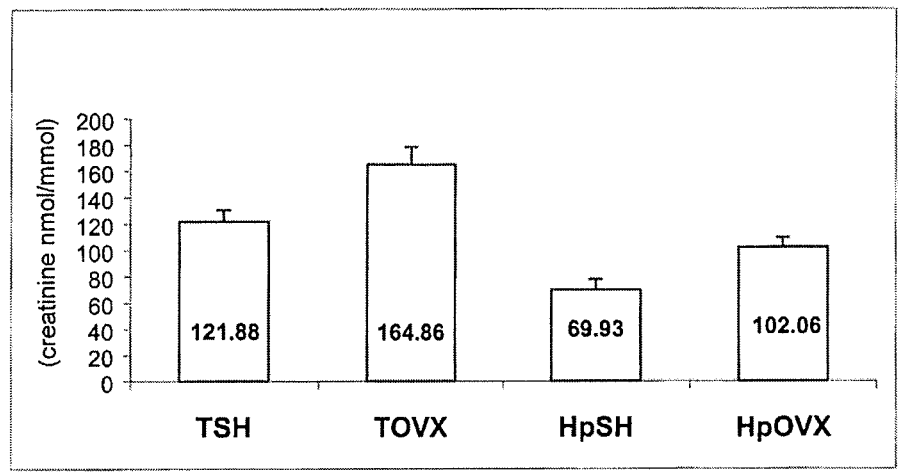
FIG. 3 illustrates the prevention, by hesperidin, of the increase of bone resorption induced by oophorectomy, evaluated by measurement of the urinary excretion of desoxypyridinoline. The measurement of the desoxypyridinoline/creatinine molar ratio in the urine is shown along the ordinate.

Urinary Excretion of Desoxypyridinoline (FIG. 3)

Oophorectomy induces a significant increase of bone resorption ($p<0.01$ vs T SH). This phenomenon is prevented by the consumption of hesperidin by the OVX rats. Similarly, in the Hp SH rats, the urinary excretion of DPD is significantly diminished in comparison with the T SH.

Figure 4:
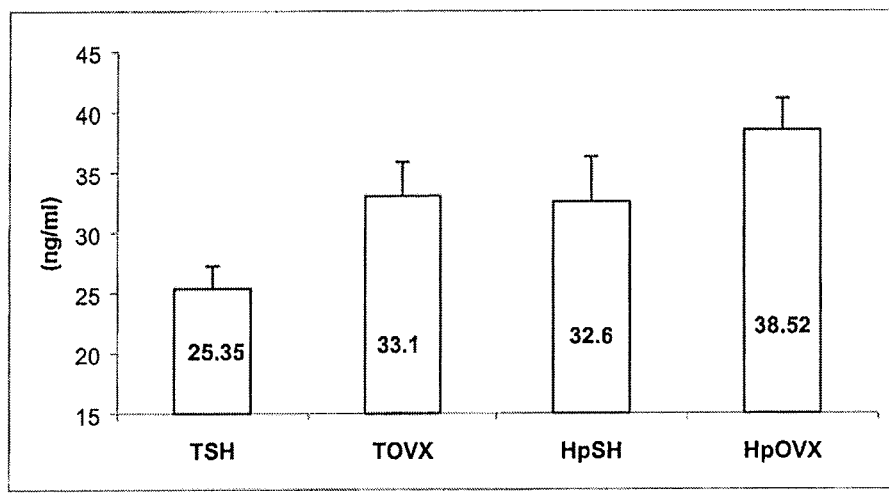
FIG. 4 illustrates the stimulation of the osteoblastic activity (evaluated by the measurement of the osteocalcin plasma levels) in the treated rats compared to the control animals. Osteocalcin plasma levels, expressed in mg/l, are shown along the ordinate.
Figure 5:
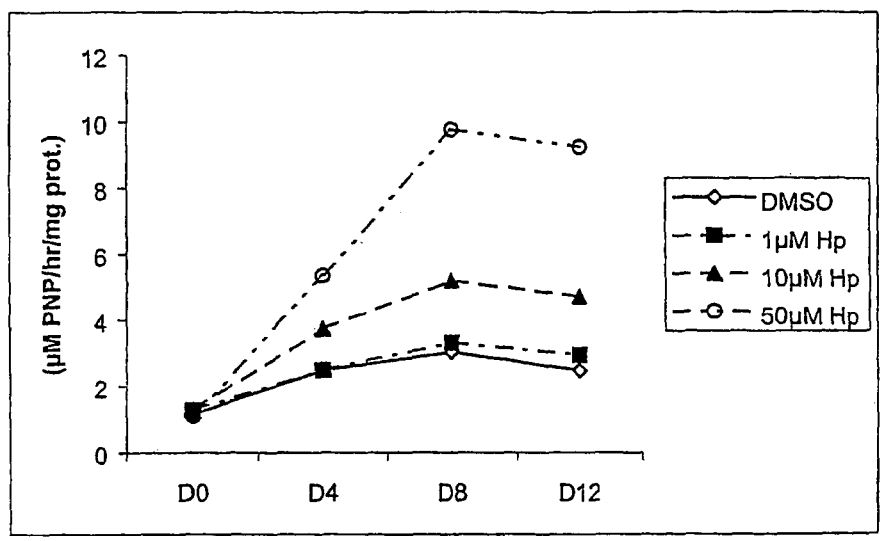
FIG. 5 illustrates the kinetics of osteoblastic differentiation (increase of the activity of alkaline phosphatase) stimulated by hesperetin at 10 and 50 µM on the hPOB-tert cells at passage 31. The alkaline phosphatase activity is expressed in µM of paranitrophenol/hour/mg of protein along the ordinate. The time expressed in days is shown along the abscissa.
Figure 6:
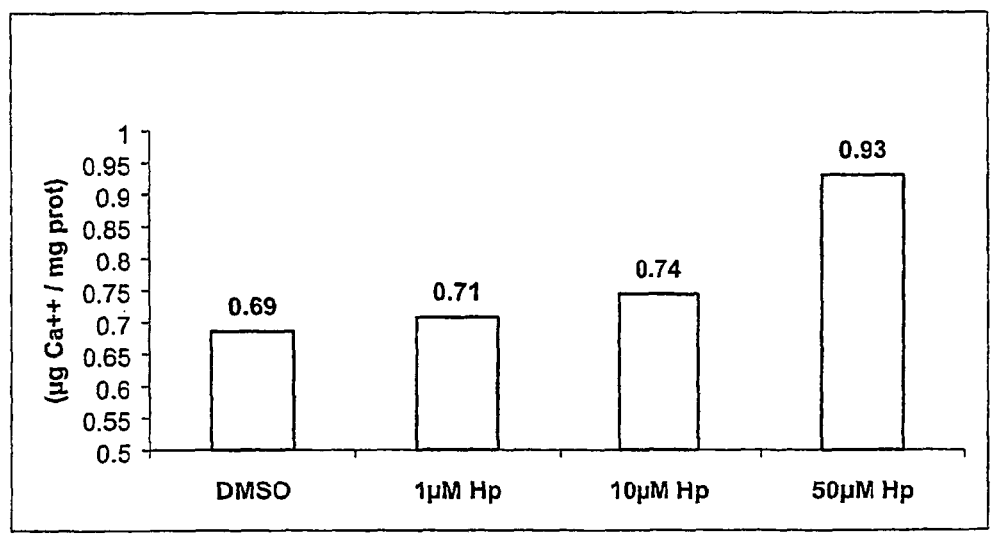
FIG. 6 illustrates the stimulation of calcium accumulation in the hPOB-tert cells (at passage 31) by hesperetin (at 50 µM), after 21 days of incubation. The measurement of the calcium$^{++}$/proteins ratio, expressed in µg Ca$^{++}$/mg proteins is plotted along the ordinate.

Plasma Levels of Osteocalcin (FIG. 4)

The consumption of hesperidin stimulates bone accretion (Hp SH vs T SH; Hp OVX vs T OVX; $p<0.05$), osteocalcin being a marker of osteoblast activity.

Circulating Levels of Hesperetin

Hesperidin is, in fact, a glycoside of hesperetin (hesperetin-7-rhamnoglucoside). The mean plasma level of aglycone found in the OVX rats, like the SH, receiving the supplementary diets of hesperidin was 12.53±2.48 μM. On the other hand, no trace of hesperetin was detected in the rats receiving the control diet.

Conclusion of Example 1

The set of results for this series of experiments indicates that hesperidin is capable of preventing bone loss following estrogen deficiency in the oophorectomised rate. This effect would seem to be due to a diminution of bone resorption coupled to an acceleration of osteoblast activity. A beneficial effect of this flavanone is even observed in intact (sham-operated) rats which thus have a hormonal status and normal bone metabolism.

Example 2

Effect of Hesperetin on hPOB-tert Cells
(Immortalised Line of Osteoblasts of Human Periosteum, Darimont et al., 2002)

We have tested three concentrations of hesperetin in the hPOB culture medium seeded to confluence: 1, 10 and 50 μM.

Furthermore, these media lacked osteoblast differentiation factors (Vitamin D3 and dexamethasone). The control contained 0.1% DMSO (hesperetin being dissolved in the DMSO). The cells were incubated in these media for 35 days. The alkaline phosphatase activity, a marker of osteoblast differentiation, was measured on a cell lysate by using a commercial kit (Sigma No 247). The cells had been harvested at 0, 4, 8 and 12 days of incubation. The calcium content of the cells, the mineralisation marker, was quantified on a cell lysate after 21 days of incubation in the different media, with the aid of a commercial kit (Sigma No587).

Results

ALP Activity

Alkaline phosphatase activity, hence osteoblast differentiation, is stimulated in a dose-dependent manner by the presence of hesperetin in the medium. The doses 10 and 50 µM increase this process from the $4^{th}$ day of experimentation onwards, a plateau being attained on the $8^{th}$ day of incubation. While 50 µM hesperetin proves to be the most efficacious, a concentration of 1 µM, on the other hand, lacks effect in comparison to the untreated cells.

Accumulation of Calcium in the Cells:

After 21 days of incubation only the 50 µM of hesperetin seems to stimulate calcium deposition, by comparison with the calcium content in the control cells (0.1% DMSO).

Example 3

Effect of Hesperidin on Bone Metabolism in the Six Months' Old Oophorectomised Rat A. Material and Methods The experiments were performed on 48 six months' old female Wistar rats: 24 oophorectomised (OVX) and 24 sham-operated (SH).

The animals were housed in individual cages at a controlled temperature of 21±1° C., according to a day-night cycle of 12 h-12 h.

After the surgical operation on D0, the animals were given seven days to accustom themselves to their surroundings. At the end of this period of adaptation, the rodents were distributed on the basis of weight parameters in 4 homogeneous groups and received daily for 72 days 22 g of the following diets:

group SH: 12 sham-operated rats fed with the control diet
group OVX: 12 oophorectomised rats which received the control diet
group SH Hp: 12 sham-operated rats fed with the hesperidin diet
group OVX Hp: 12 oophorectomised rats which received the hesperidin diet When sacrificed (D90), the animals were anesthetised by an intra-peritoneal injection of chloral (Fluka: 8% solution; 0.4 ml/100 g live weight). Blood samples were collected from the abdominal aorta. The uterus was weighed.

The femurs were extracted and adjacent soft tissues were removed, then the femurs were stored in 80% ethanol for the determination of bone density.

B. Results

1. Foodstuff Consumption

The quantity of foodstuff distributed was calculated on the basis of the level of the lowest mean consumption the week preceding the experiment (group SH)

Figure 7:
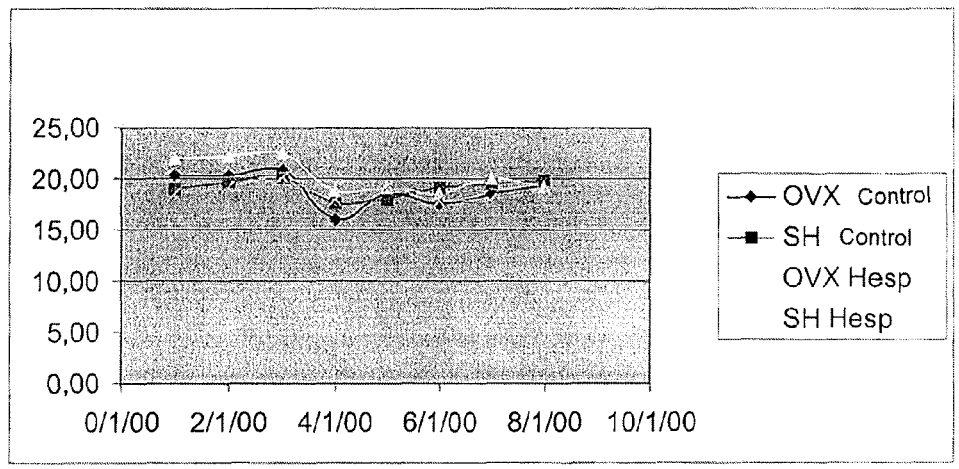
FIG. 7 illustrates the control of the food uptake with time in oophorectomised rats untreated (OVX control) or treated with hesperidin (OVX Hesp) and in normal rats untreated (SH control) or treated with hesperidin (SH Hesp). Along the abscissa: time in two day intervals; along the ordinate: grams of foodstuff consumed.

The results are presented in FIG. 7.

The results in FIG. 7 show that no significant difference was observed at the level of the feeding of the animals of the different groups.

2. Weight Change

Figure 8:
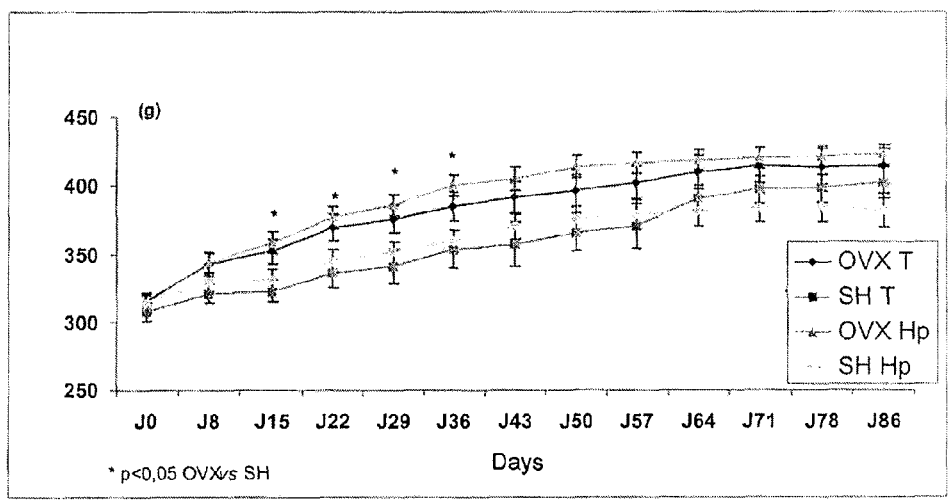
FIG. 8 illustrates the profile of the change in weight of the rats in the groups (SH), (SH Hesp), (OVX) and (OVX Hesp). Along the abscissa: number of days; along the ordinate: mean weight of the animals+/− standard deviation.

The results of weight change are presented in FIG. 8.

The weight profile of the animals of all the groups show a similar pattern of change, namely an increase between the start and the end of the experiment, irrespective of the group considered.

3. Body Composition

Figure 9:
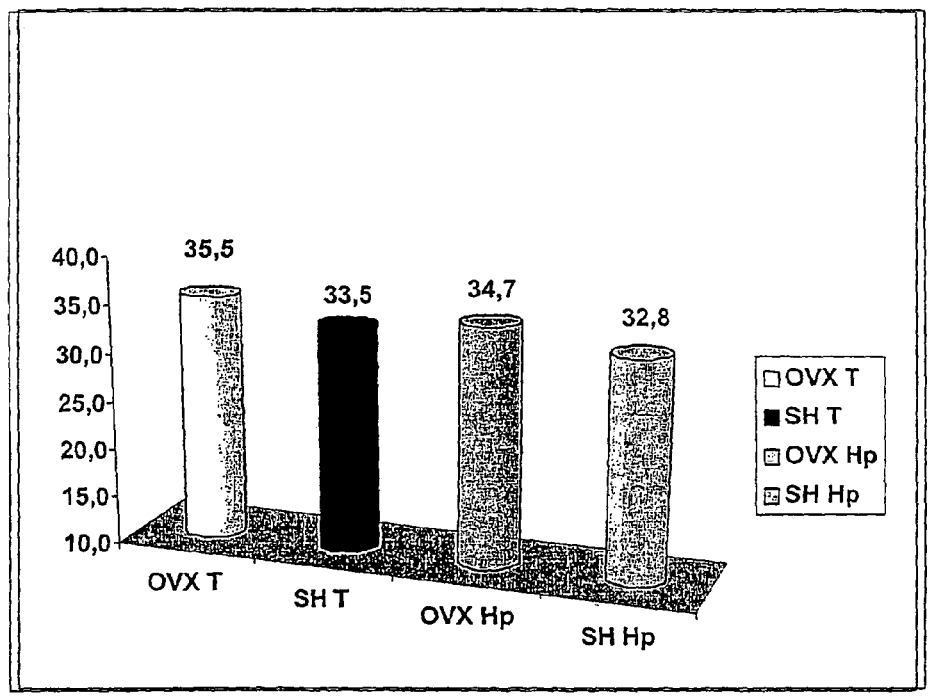
FIG. 9 illustrates the body composition, as percentage of fat mass, of the rats in the batches (SH), (SH Hesp), (OVX) and (OVX Hesp). Along the abscissa: group of animals; along the ordinate: body composition, expressed in percentage of fat mass.

The results of the measurement of body composition are presented in FIG. 9.

The body composition of the animals in the different groups was not significantly modified, irrespective of the treatment undergone by the individuals.

4. Uterine Weight

Figure 10:
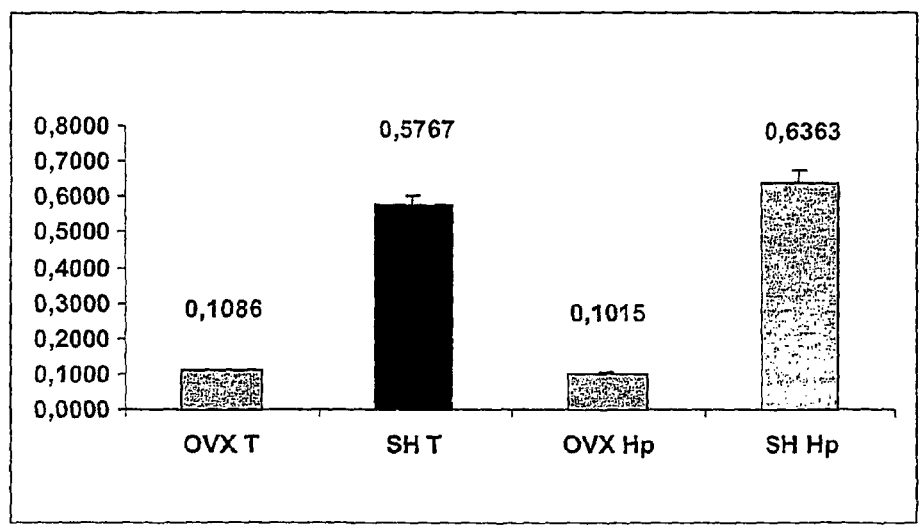
FIG. 10 illustrates the weight of the uterus of the rats in the groups (SH), (SH Hesp), (OVX) and (OVX Hesp). Along the abscissa: group of animals; along the ordinate: mean weight of the uteri, expressed in grams.

The results are presented in FIG. 10.

Uterine atrophy following ovarian ablation is not prevented by the consumption of hesperidin.

The results presented in FIG. 10 thus show that hesperidin lacks a uterotrophic effect.

5. Bone Mineral Density

Figure 11:
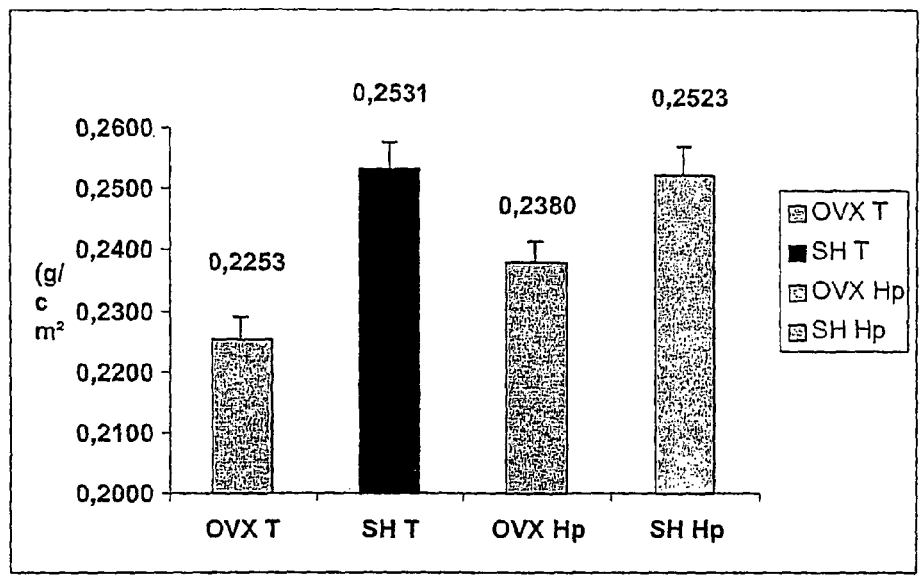
FIG. 11 illustrates the total femoral density (T-BMD) in the rats in the groups (SH), (SH Hesp), (OVX) and (OVX Hesp). Along the abscissa: group of animals; along the ordinate: femoral mineral density, expressed in $g/cm^2$.
Figure 12:
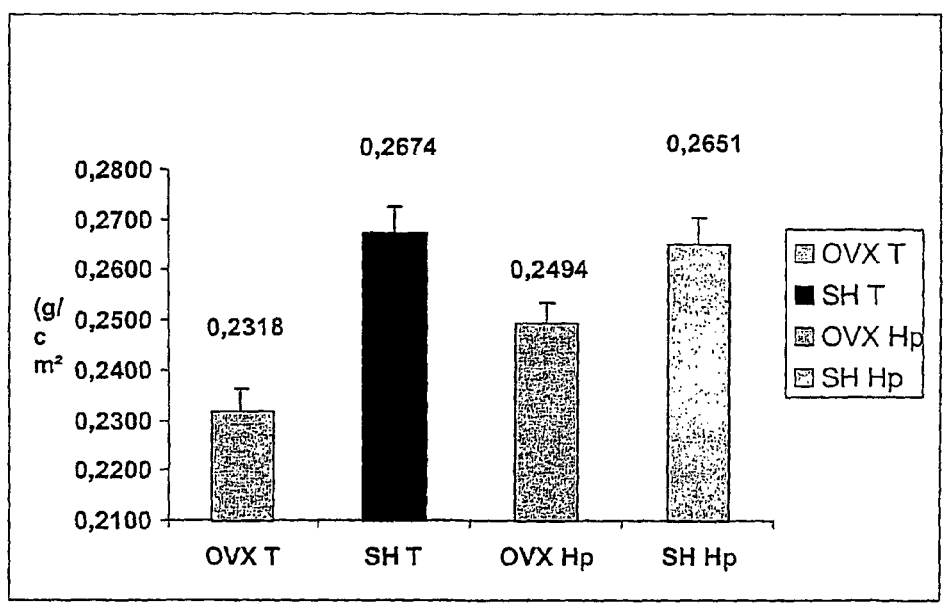
FIG. 12 illustrates the mineral density of the femoral proximal metaphysis (M-BMDp) in the rats in the groups (SH), (SH Hesp), (OVX) and (OVX Hesp). Along the abscissa: group of animals; along the ordinate: mineral density of the femoral proximal metaphysis, expressed in $g/cm^2$.
Figure 13:
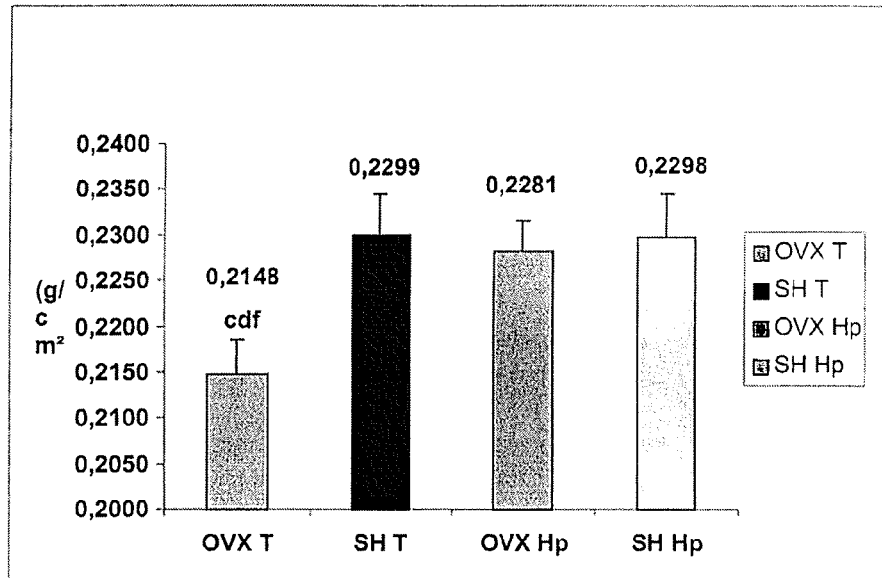
FIG. 13 illustrates the femoral diaphyseal mineral density (D-BMD) in the rats in the groups (SH), (SH Hesp), (OVX) and (OVX Hesp). Along the abscissa: group of animals; along the ordinate: femoral diaphyseal mineral density, expressed in $g/cm^2$.

The results of the measurement of bone mineral density are presented in the FIGS. 11, 12 and 13. The results of the measurement of the total femoral mineral density are presented in FIG. 11. The results of the measurement of the mineral density of the femoral proximal metaphysis are presented in FIG. 12. The results of the measurement of the femoral diaphyseal mineral density are presented in FIG. 13.

Castration results in a demineralisation of the femur, demonstrated by a reduced total bone mineral density (g/cm$^2$). This process is prevented (at least partially) by the consumption of hesperidin. A similar profile is demonstrated at the trabecular level (FIG. 12), as well as in the cortical bone (FIG. 13).

6. Biomechanical Properties

Figure 14:
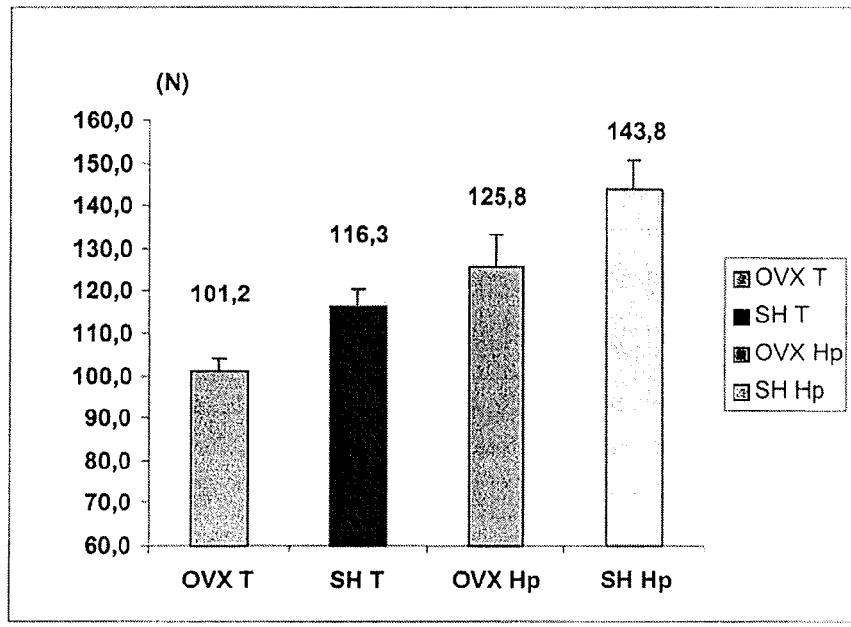
FIG. 14 illustrates the femoral load at rupture in the rats in the groups (SH), (SH Hesp), (OVX) and (OVX Hesp). Along the abscissa: group of animals; along the ordinate: femoral load at rupture, expressed in Newtons (N).

The mechanical properties of the femur of the individuals of the different groups of animals were analysed. The results are presented in FIG. 14.

The biomechanical properties of the femur have deteriorated as a result of the estrogen deficiency. The consumption of hesperidin (OVX Hp) made it possible to preserve them, and even improve them in the intact animals.

In conclusion, the results for Example 3 show that hesperidin possesses an osteoprotective activity in an experimental model of bone loss linked to ageing.

The invention claimed is:

1. A method for stimulating bone formation and/or inhibiting bone resorption in man or animals comprising a step of administering to a subject in need thereof, an effective amount of a composition consisting essentially of containing hesperidin or a derivative thereof selected from the group consisting of alpha-glucosyl-hesperidin, methyl hesperidin, a conjugate of hesperitin and sulphate and a conjugate of hesperitin and glucuronide as active ingredients.

2. The method according to claim 1, wherein said composition consists of a nutritional composition suitable for oral administration.

3. The method according to claim 2, wherein said nutritional composition is designed to stimulate bone formation in young individuals in the growth phase.

4. The method according to claim 2, wherein said nutritional composition is designed to reduce an imbalance in bone remodelling which occurs with ageing.

5. The method according to claim 2, wherein said nutritional composition is designed to reduce an imbalance in bone remodelling or treat disorders linked to an imbalance in the relationship between bone formation and bone resorption.

6. The method according to claim 2, wherein said nutritional composition is designed to treat a bone deficit resulting from a fracture.

7. The method according to claim 2, wherein said nutritional composition is designed to reduce an imbalance in bone remodelling or treat a disease selected from osteoporosis, Paget's disease, bone loss or osteolysis observed close to a prosthesis, metastatic bone diseases, hypercalcemia due to a cancer, multiple myelomas, periodontal diseases or osteoarthritis.

8. The method according to claim 2, wherein said nutritional composition is in the form of drinks, juices, yoghurts, ice creams, cheeses, baked products, bread, biscuits and cakes, dairy products, desserts, confectionery products, cereal bars, breakfast cereals, food seasoning products, fruit salads or stewed fruit.

9. The method according to claim 2, wherein said nutritional composition is in the form of a product designed for animal feed, in a wet, semi-wet or dry form.

10. The method according to claim 2, wherein the compound hesperidin or one of its derivatives is available in the form of an extraction product obtained from the peel or the pulp of a citrus fruit.

11. The method according to claim 2, wherein said nutritional composition is adapted for oral administration of a daily quantity included between 0.01 and 500 mg of the compound hesperidin or of one of its derivatives.

12. The method according to claim 1, wherein said composition consists of a human pharmaceutical or veterinary composition.

13. The method according to claim 12, wherein said pharmaceutical composition is designed to stimulate bone formation in the young individual in the growth phase.

14. The method according to claim 12, wherein said pharmaceutical composition is designed to reduce an imbalance in bone remodelling which occurs in the course of ageing.

15. The method according to claim 12, wherein said pharmaceutical composition is designed to reduce an imbalance in bone remodelling or treat a disease linked to an imbalance in the relationship between bone formation and bone resorption.

16. The method according to claim 12, wherein said pharmaceutical composition is designed to treat a bone deficit resulting from a fracture.

17. The method according to claim 12, wherein said composition is designed to reduce an imbalance in bone remodelling or treat a disease selected from osteoporosis, Paget's disease, bone loss or the osteolysis observed close to a prosthesis, metastatic bone diseases, the hypercalcemia due to a cancer, multiple myelomas, periodontal diseases or osteoarthritis.

18. The method according to claim 12, wherein said pharmaceutical composition is in a form for oral, parenteral or intravenous administration.

19. The method according to claim 12, wherein the pharmaceutical composition is suitable for an oral administration of a daily quantity included between 0.01 and 500 mg of the compound hesperidin or of one of its derivatives.

20. The method according to claim 8, wherein the nutritional composition is available in the form a fruit juice.

* * * * *